(12) United States Patent
Pedersen (10) Patent No.: US 10,722,656 B2
(45) Date of Patent: Jul. 28, 2020

(54) PISTON ROD DRIVE FOR AN INJECTION DEVICE

(71) Applicant: Novo Nordisk A/S, Bagsvaerd (DK)

(72) Inventor: Simon Munch Pedersen, Copenhagen N (DK)

(73) Assignee: Novo Nordisk A/S, Bagsvaerd (DK)

(*) Notice: Subject to any disclaimer, the term of this patent is extended or adjusted under 35 U.S.C. 154(b) by 306 days.

(21) Appl. No.: 15/543,405

(22) PCT Filed: Jan. 25, 2016

(86) PCT No.: PCT/EP2016/051399
§ 371 (c)(1),
(2) Date: Jul. 13, 2017

(87) PCT Pub. No.: WO2016/120180
PCT Pub. Date: Aug. 4, 2016

(65) Prior Publication Data
US 2018/0001030 A1    Jan. 4, 2018

(30) Foreign Application Priority Data
Jan. 28, 2015  (EP) ..................... 15152905

(51) Int. Cl.
*A61M 5/315*    (2006.01)
*A61M 5/20*    (2006.01)

(52) U.S. Cl.
CPC .......... *A61M 5/31501* (2013.01); *A61M 5/20* (2013.01); *A61M 5/31535* (2013.01); *A61M 5/31583* (2013.01); *A61M 5/2033* (2013.01); *A61M 2005/31508* (2013.01); *A61M 2005/31588* (2013.01)

(58) Field of Classification Search
CPC .............. A61M 5/315; A61M 5/31501; A61M 5/31511; A61M 5/31513; A61M 5/31525; A61M 5/31583; A61M 2005/3152; A61M 2005/31508
See application file for complete search history.

(56) References Cited

U.S. PATENT DOCUMENTS 6,004,297 A    12/1999  Steenfeldt-Jensen et al.
2007/0017512 A1  1/2007  Peter et al.
(Continued)

FOREIGN PATENT DOCUMENTS

CN    202802378 U    3/2013
DE    102006038101 A1  2/2008
(Continued)

*Primary Examiner* — Lauren P Farrar
*Assistant Examiner* — James D Ponton
(74) *Attorney, Agent, or Firm* — Wesley Nicolas (57) ABSTRACT

The invention relates to a piston rod drive arrangement for an injection device used for self-administration of a plurality of individually set doses. The drive arrangement is made from a first element (10) mating the non-circular cross-section (3) of a piston rod (1) and a second element (20) having an inner thread (21) mating the outer thread of the piston rod. Whenever the first element (10) and the second element (20) are rotated in relation to each other the piston rod (1) is moved in an axial direction. In order to minimise the play in the threaded connection a resilient element (23) is proved to apply a force to the piston rod (1) in a longitudinal direction.

11 Claims, 4 Drawing Sheets (56) References Cited

U.S. PATENT DOCUMENTS

2012/0083748 A1\* 4/2012 Harms .............. A61M 5/31525
  604/224
2014/0107587 A1 4/2014 Hogdahl

FOREIGN PATENT DOCUMENTS

| EP | 1003581 | 8/1999 |
| JP | 2010509956 A | 4/2010 |
| WO | 2008058665 A1 | 5/2008 |
| WO | 2010029043 A1 | 3/2010 |
| WO | 2014060369 A1 | 4/2014 |

\* cited by examiner

Distal ←

PISTON ROD DRIVE FOR AN INJECTION DEVICE

CROSS-REFERENCE TO RELATED APPLICATIONS

This application is a 35 U.S.C. § 371 National Stage application of International Application PCT/EP2016/051399 (published as WO 2016/120180), filed Jan. 25, 2016, which claims priority to European Patent Application 15152905.4, filed Jan. 28, 2015; the contents of which are incorporated herein by reference.

THE TECHNICAL FIELD OF THE INVENTION

The invention relates to a piston rod drive arrangement for an injection device, especially for an injection device for self-administration of variable set doses of a liquid drug. The invention especially relates to the reduction, or removal, of any play, in particular axial play, in such piston rod drive arrangement. The invention also relates to an injection device utilizing such piston rod drive arrangement.

DESCRIPTION OF RELATED ART

EP 1,003,581 discloses a pre-filled injection device having a piston rod drive arrangement. The injection device depicted in FIG. 15-17 is successfully sold by the company Novo Nordisk A/S under the trade name Flexpen®.

As best seen in FIG. 17, the piston rod drive arrangement comprises a piston rod (6) having a helical outer thread and a non-circular cross-section in the form of two longitudinal flat recesses. In order to rotate the piston rod, a first element (85) mating the non-cross section engages the piston rod and the outer thread of the piston rod is engaged by an internal thread moulded in a nut member (40). This nut member is firmly secured in the housing such that whenever the first element is rotated, the piston rod rotates with it and is thus screwed forward in the thread of the nut member.

In order to rotate the first element during expelling of a set dose, a dose setting and expelling mechanism is provided. When this mechanism is operated to expel a dose, the first element is rotated and the piston rod henceforth moves in the distal direction in a helical movement.

Both the nut member and the piston rod are moulded from a suitable polymeric material and when moulding plastic components certain tolerances apply. Since it is desired not to have to tight an engagement in the thread connection these tolerances need to be relatively high. This however provides a certain play in the threaded connection between the piston rod and the nut member which negatively impacts the dose accuracy of the drive arrangement.

This is especially critical in drive arrangement of the type in which the piston rod is released to float between injections. Such a piston rod drive arrangement is e.g. described in WO 2014/060369. In this drive system, the drive member and thus the piston rod are free to rotate at all times except when a dose is being released i.e. only during dosing is the drive member rotational locked. Since the rotorical position is unknown when engaging, it is important to level out any play in the threaded connection between the nut element and the piston rod.

WO 2014/060369 further discloses a connection between a piston rod foot and a piston rod which is able to reduce or eliminate axial play between the piston rod foot and the piston rod however this does not influence on the tolerance created play between the outer thread of the piston rod and the inner threaded of the nut member engaging the piston rod.

DESCRIPTION OF THE INVENTION

It is an object of the present invention to provide a piston drive arrangement in which any play in the threaded connection making up the drive arrangement has been at least reduced and preferably removed.

Accordingly, in one aspect of the present invention, a piston rod drive arrangement for an injection device is provided which comprises:

A piston rod having an outer surface with an outer thread which extends helically in a longitudinal direction. The longitudinal direction preferably coincides with the centre line of the piston rod of the injection device into which the piston rod arrangement is build. The piston rod further has a longitudinal engagement surface thus giving the piston rod a non-circular cross-section.

A first element which mate the non-circular cross-section of the piston rod by engaging the longitudinal extending engagement surface provided on or in the piston rod.

A second element having an inner thread mating the outer thread of the piston rod.

Whenever the first element and the second element are rotated in relation to each other, the piston rod is moved axially.

According to the invention, the piston rod drive arrangement is further provided with a resilient element, which applies a force onto the piston rod in the longitudinal direction.

The non-circular cross section of the piston rod is meant to be any kind of cross-section that can be engaged by the first element to form a locking engagement such that the piston rod is unable to rotate relatively to the first element. All though a piston rod with an outer thread, academically speaking could be said to have a non-circular cross section it is herein meant that the non-circular cross section constitutes a longitudinal extending engagement surface which can be engaged by the first element to lock the piston rod rotational to the first element but to allow relative axial movement. Such engagement is e.g. known from EP 1,003,581 which discloses that the piston rod has a number of longitudinal recesses or flat sides which is engaged by the first element having a similar geometrical shape.

However, the engagement between the piston rod and the first element could alternatively be a longitudinal groove carved in the piston rod and engaged by a protruding part internally in the first element. Alternatively, the non-circular cross section of the piston rod could be a radial extension which thus makes up the longitudinal extending engagement surface engaged by a similar inwardly protruding flange or the like provided in the first element. Such radial extension could be provided as a plurality of radial extensions located on the top of the helical thread of the piston rod as will be explained later.

By applying a force onto the piston rod in one and the same direction in all situations such that the thread of the piston rod axially abuts the thread of the nut member any play can be significantly reduced and even removed. The resilient element is located such that the force is applied in an axial direction i.e. in a lengthwise direction and preferably onto the flange or crest of the outer thread of the piston rod of the injection device. Since the thread of the piston rod is made up from a helical groove or root surrounded by a helical flange or crest, the resilient element preferably apply the pressure onto the crest thus pushing the piston rod axially in the distal or the proximal direction. One side of the helical crest is thereby permanently pushed towards a side of the inner thread of the second element.

The resilient element applying the axial force is preferably provided on the first element or on the second element. In one preferred example the resilient element is formed integral with the second element and preferably as an integral part of the inner thread of second element.

The inner thread is preferably formed from a number of segments of a thread which together make up a virtual thread. By a thread segment is meant a part of a thread which provide the helix of the thread but which covers less than one full rotation of the thread. Such segment can even be a simple plurality of protrusions which is axially displaced to introduce the helix angle of the virtual thread created by the protrusions.

If the thread segment has a peripheral form only one segment actually needs to be present. This one thread segment thus only needs cover a few degrees such that it just introduces the helix angle of the virtual thread introduced by the one segment. However, in order to obtain a stabile axial movement of the piston rod it is preferred to use at least two thread segments which in a preferred embodiment together cover the majority of the 360 degrees of a full thread rotation.

In a further example, the resilient member is formed as an integral part of the inner thread of the second element. When the inner thread is formed from one or more thread segments as explained above, one or more of these thread segments preferably carries the resilient member.

In one example, the resilient members are formed as a peripheral extension of the thread segment. If more than one thread segment is present only one of the thread segments actually needs to be provided with a peripheral extension. However, any number of thread segments can be present and any of these thread segments can be provided with such peripheral extension. The peripheral extension preferably has the shape of an arm extending one or more thread segments in the peripheral direction. The thread segment thus terminates in such arm which has a certain resiliency. The arm preferably has a different helix angle than the body of the thread segment such that the arm deflect from the pitch of the thread segment and abut the crest of the outer thread of the piston rod in order to apply an axial force onto the piston rod. This axial force thus presses the crest of the outer thread of the piston rod against the crest of the thread segment thereby eliminating any play between the crest of the two engaging threads.

In one preferred example if e.g. two thread segments are provided each terminating in a resilient arm, the pitch of the two arms are slightly different from the pith of the body of the two thread segments, or in other words, the body of the thread segments and the resilient arms has different helix angles.

By using two, three or four thread segments each having a resilient arm the force is evenly distributed onto the crest of the outer thread of the piston rod.

The outer thread of the piston rod is preferably unbroken such that the axial force delivered by the resilient element is delivered throughout the full rotation of the piston rod. If the non-circular cross section of the piston rod was provided as two longitudinal flat recesses as described in the prior art, the resilient element, if formed as resilient arms, would get caught by the flat recesses. It is therefore necessary to make the thread of the piston rod unbroken at least when the resilient element is formed as resilient arms. However, other solutions using a different kind of resilient elements could be implemented.

If e.g. two resilient arms are present, the longitudinal extending engagement surfaces could be provided such that at least one resilient arm at a time applies a longitudinal pressure onto the crest of the piston rod.

The non-circular cross-section of the threaded piston rod is in an unbroken version provided as a series of knobs extending radially from the top of the outer thread. These knobs preferably extend from the top of the unbroken flange or crest of the outer thread in a direction perpendicular to the longitudinal direction of the piston rod and thus the injection device. The knobs in a series are preferably provided following a line running in parallel with the longitudinal direction. Any number of series of knobs can be provided and each knob in a series has a well-defined side surface such that the side surfaces of all the knobs in one series form segments of a engagement surface stretching in parallel with the longitudinal direction.

The first element preferably engages the longitudinal extending engagement surface made up by the series of knobs such that rotation of the first element is transferred to the side surfaces of the knobs in a series and thus to rotation of the piston rod. In the embodiment in which the first element is kept stationary, the engagement between the first element and the series of knobs prevents the piston rod from rotating.

In order to properly transfer force from the first element and onto the series of knobs, the first element is preferably provided with a rigid flange running in parallel with the longitudinal direction of the piston rod.

In order to engage and rotate the side surface of the series of knobs properly against the rigid flange on the first element, the first element is in one example provided with a resiliency urging the side surface of the series of knobs against the rigid flange.

The resiliency is preferably formed as a resilient arm attacking the series of knobs on one side thus urging the opposite side surface of the series of knobs against the rigid flange.

The invention further relates to an injection device for self-administration of a plurality of individually set doses. Such injection device could in one example be an automatic spring-loaded pre-filled injection device.

The three different elements of the piston drive arrangement; the piston rod, the first element and the second element is able to transform rotational movement to axial movement of the piston rod in either of two different ways as explained. This can be utilized in an injection device as referred to in claim 10 and claim 11

In the embodiment of claim 10, the injection device comprises:

A housing securing a drug container and a piston rod drive arrangement as herein described wherein the first element is non-rotatable secured in the housing and the second element is rotatable. Henceforth when rotating the second element which is threadedly connected to the piston rod, the piston rod is moved axially without rotating. As the first element is kept inrotatable, it also keeps the piston rod inrotatable thus the rotation of the second element is transferred to a purely axial movement of the piston rod.

In the embodiment of claim 11, the injection device comprises:

A housing securing a drug container and a piston rod drive arrangement as herein described, but wherein, the second element is non-rotatable secured in the housing and the first element is rotatable. Henceforth when rotating the first element, the piston rod follows this rotation and is moved axially and rotational in the inner thread of the second element which second element is rotationally locked to the housing thus the rotation of the first element is transferred to a rotational and axial (i.e. helical) movement of the piston rod.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Injection Needle" is used to describe the instrument used for performing the penetration of the skin during injection. Such injection needle often comprises a needle cannula made from a metallic material such as e.g. stainless steel and connected to a hub to form a complete injection needle.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out.

Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the piston rod pointing toward the user during injection, and which end carries a piston rod foot whereas the term "proximal end" is meant to refer to the opposite end pointing away from the user during injection. Distal and proximal is meant to be along an axial orientation of the piston rod along a virtual centre line marked "X" in FIG. 1 which discloses the piston rod drive arrangement according to a first embodiment.

Figure 5:
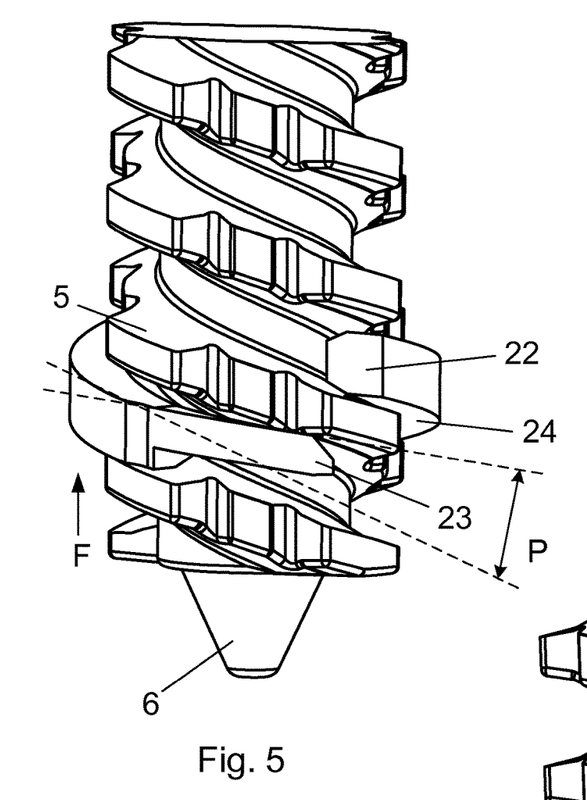
FIG. 5 show a perspective view of the engagement between the thread segment of the second element and the outer thread of the piston rod.
Figure 6:
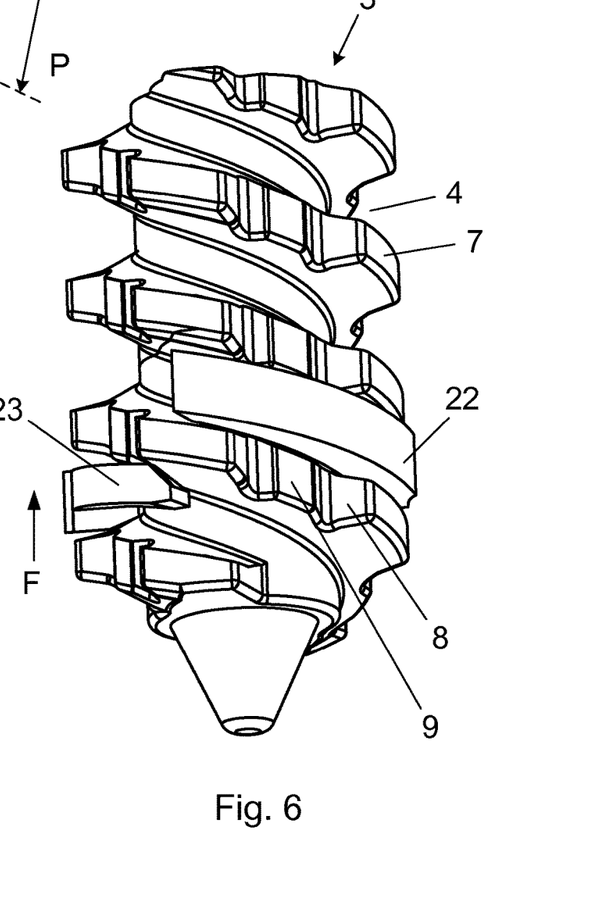
FIG. 6 show the perspective view of FIG. 5, viewed from a different angle.

The piston rod 1 is a rod-shaped element carrying a helical outer thread 2 and a non-circular cross section 3 as best seen in FIGS. 5 and 6.

Figure 1:
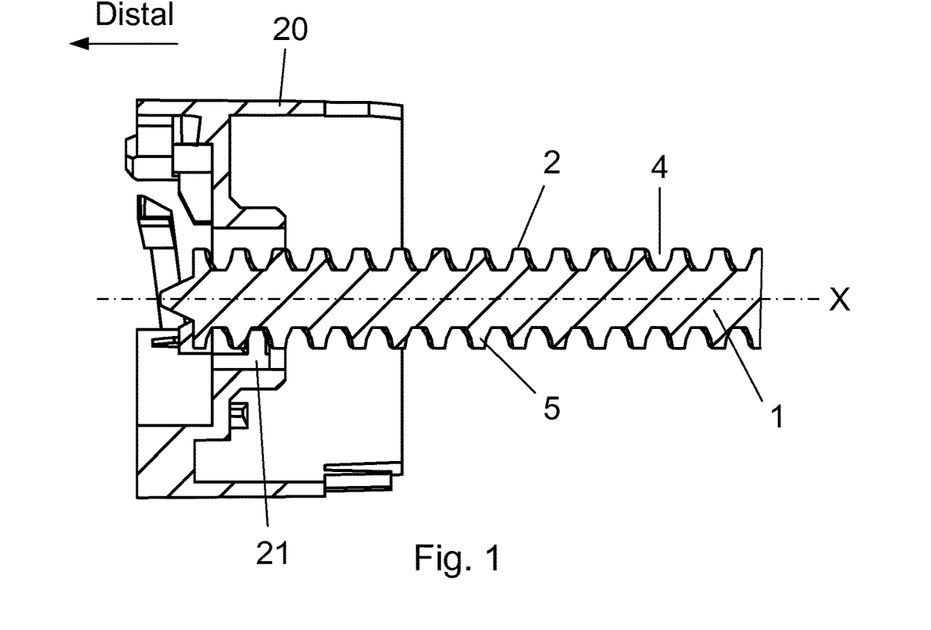
FIG. 1 show a cross sectional view of the threaded connection between the piston rod and the second element.
Figure 2:
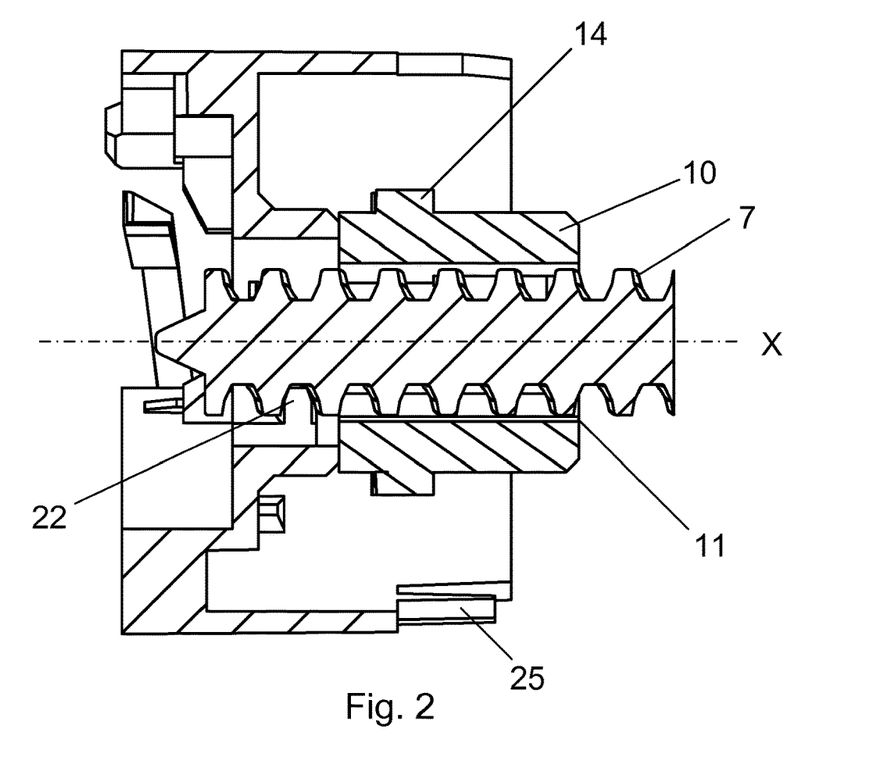
FIG. 2 show the cross sectional view of FIG. 1 with the first element engaging the piston rod.

The piston rod 1 has both an axial or longitudinal direction and a radial direction extending perpendicular to the axial or longitudinal direction. By being rod-shaped is meant that the piston rod has a generally circular outer surface and extends much longer in the longitudinal direction than in the radial direction. The longitudinal direction follows along the centre line which in FIGS. 1 and 2 is indicated by a broken line (X) and the helical outer thread (2) extend helically in the longitudinal direction. The outer thread 2 need not be formed in the entire length of the piston rod 1 as disclosed but can be present only in a limited longitudinal part of the piston rod 1. Further, the piston rod 1 can be provided with more than one helical outer thread 2 which can even be of different pitches. The pitch of a thread is meant to be the distance between the thread crests. The crest is the helically extending top of the thread, which is separated by the root in the longitudinal direction.

The non-circular cross section of the piston rod 1 can be provided in many different ways. In one example it can be one or more longitudinal extending track(s) carved into the surface of the piston rod 1 or it can be that the outer circular surface of the piston rod is flatten on one or more side(s). In a preferred embodiment the non-circular cross section is provided as a radial extending engagement surface or flange provided on top of an unbroken outer thread 2 as will be explained.

The second element 20 is provided with an inner thread 21 which mates the outer thread 2 of the piston rod 1 such that the outer thread 2 of the piston rod 1 is able to rotate in the inner thread 21 like a nut and bolt engagement In an injection device, the liquid drug is usually stored in a container such as e.g. a glass cartridge, which is proximally closed by a movable rubber plunger. During injection the piston rod 1 moves towards the left (i.e. in the distal direction as seen in FIG. 1 and FIG. 2) such that the conical tip 6 of the piston rod 1 moves the rubber plunger further into the cartridge. The conical tip 6 of the piston rod 1 usually carries a not-shown piston rod foot to properly distribute the force onto the rubber plunger of the cartridge. In the FIGS. 1 and 2, the centre line (X) of the piston rod 1 defines the axial or longitudinal direction.

As disclosed in FIG. 1, the longitudinal extending piston rod 1 can be moved forward in the distal direction in two different ways;

a) The second element 20 can be secured rotational i.e. such that the second element 20 is prevented from rotating, while the piston rod 1 is rotated. This will screw the piston rod 1 rotational forward in a helical movement.
   b) Alternatively, the second element 20 can be rotated while the piston rod 1 is maintained non rotational. This will move the piston rod 1 strictly axially forward without rotating the piston rod 1.

In order to either rotate the piston rod 1 or to secure it rotational, a first element 10 is provided as disclosed in FIG. 2. This first element 10 has an internal shape 11 mating with the non-circular cross section 3 of the piston rod 1. This internal shape 11 can be any kind of shape that engages with the non-circular cross section 3 of the piston rod 1.

In the above solution a); the first element 10 engages and rotates the piston rod 1, whereas in the above example b); the first element 10 engaging the piston rod 1 is kept stationary while the second element 20 is rotated.

The non-circular cross section 3 of the piston rod 1 is formed as a longitudinal extending engagement surface provided in or on the piston rod 1 such that the first element 10 is able to engage this longitudinal extending engagement surface.

In a preferred embodiment the non-circular cross section 3 of the piston rod 1 is made as a series of radial knobs 7, 9 provided on the top of the helical crest 5 making up the outer thread 2 of the piston rod 1, and the internal shape 11 of the first element 10 is made as a rigid flange 12 abutting a series of knobs 7, 9 as will be explained.

In one embodiment, the second element 20 is non-rotational secured in the housing of the injection device, e.g. by having click-arms 25 which are press fitted into similar grooves in the housing, or by the housing having a protruding part engaging the area surrounding the click-arms 25. Alternatively, the second element 20 can be formed integral with the housing, whereas the first element 10 can be rotated e.g. by a spring engine. The rotation of the first element 10 is thus transformed to a similar rotation of the piston rod 1 which is thus brought forward in the distal direction in a combined rotational and axial movement i.e. a helical movement.

In the embodiment depicted in FIG. 1 and in FIG. 2, the inner thread 21 of the second element 20, is actually made up from two thread segments 22 having a certain pitch, whereas the outer thread 2 of the piston rod 1, is provided as a helical root 4 surrounded by a helical crest 5 which is unbroken as will be explained later.

However, all though FIG. 1 uses the reference number "21" to illustrate the inner thread, all the figures actually depicts the inner thread as two thread segments indicated by the reference number "22".

If the thread 21 of the second element 20 is an ordinary and well-known thread having a constant pitch, a small axial (and non-rotational) movement of the piston rod 1 is possible since there is a small axial clearance between the thread segments 22 thread 21 and the root 4 defining the thread connection between the second element 20 and the piston rod 1. The size of this axial clearance is the result of the moulding tolerances, but since the thread connection should not operate to tight, these tolerances are usually chosen such that a little axial clearance is present.

In order to eliminate the clearance an axial force is, according to the present invention, applied to the piston rod 1 such that the crest 5 of the helical thread 2 is pressed against the thread segments 22.

Figure 3:
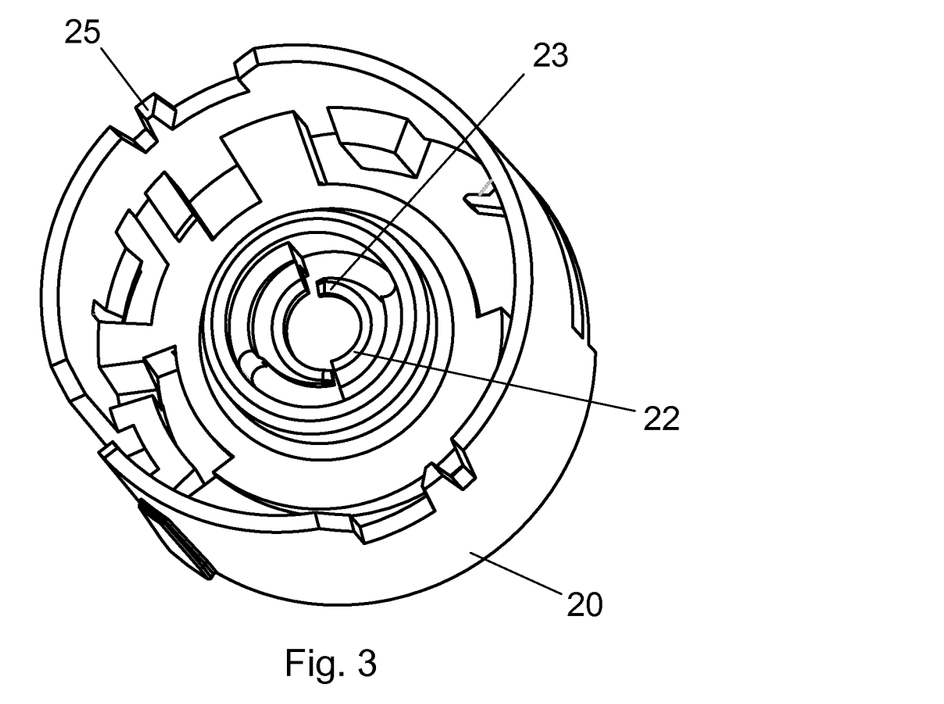
FIG. 3 show a perspective view of the second element.
Figure 4:
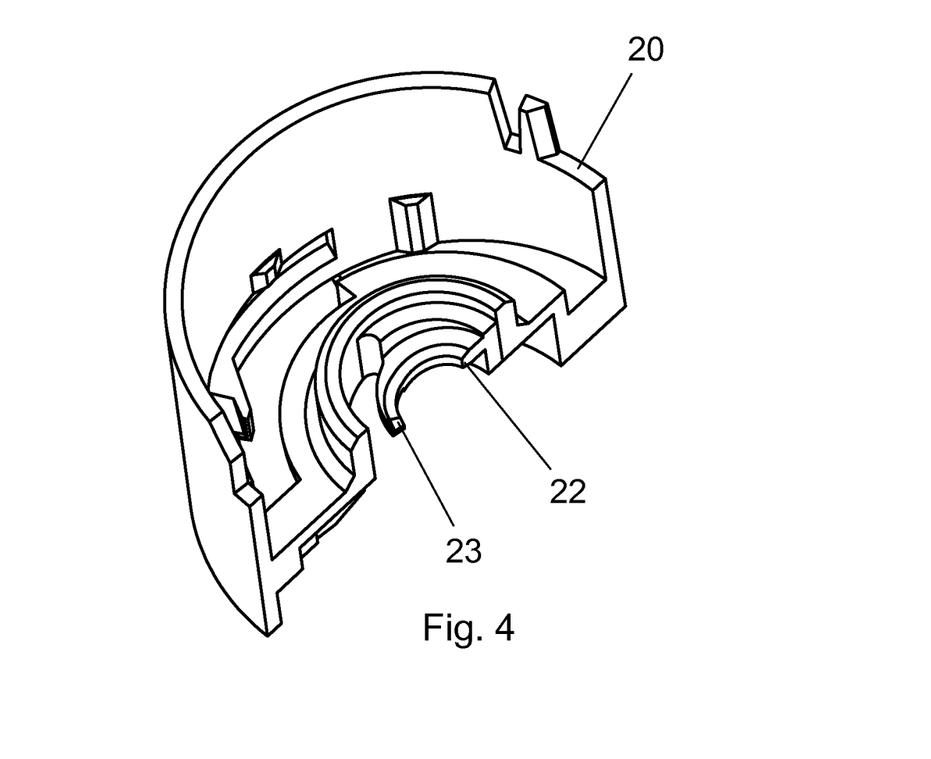
FIG. 4 show a perspective view of the second element cut into half.

As disclosed in FIGS. 3 and 4, each thread segment 22 of the second element 20 is peripherally provided with a peripheral and resilient arm 23 which makes up an integral part of the thread segment 22. As best seen in FIG. 3, two such segments 22 each having a peripheral arm 23 are preferred.

As best seen in FIG. 5-6, the resilient arm 23 of each thread segment 22 is moulded such that the arm 23 each has a pitch angle that slightly deviates from the pitch angle of the thread segment 22 carrying the resilient arm 23. This is e.g. indicated with a "P" in FIG. 5. The axial distance between the peripheral end of the resilient arm 23 and the remaining part of the thread segment 22 is thus smaller than the actual pitch of the thread as indicated in FIG. 5. The pitch of the outer thread 2 of the piston rod 1 and the inner thread of the thread segment 22 are preferably the same with the resilient arm 23 narrowing the gap there between.

The resilient arm 23 thus applies an axial force to the crest 5 and urges the piston rod 1 in the proximal direction such that the opposite side surface of the crest 5 of the helical outer thread 2 is pressed against a distal side surface 24 of the thread segment 22. Since the force (indicated with "F" in FIG. 5 and in FIG. 6) always apply a light pressure on the piston rod 1 in the proximal direction any play in the threaded connection can be avoided. However, the axial direction of the force F can be in either of the axial directions.

Since the force F is applied onto the helical crest 5 of the outer thread 2, this helical crest 5 needs to be unbroken. Otherwise the force F of the resilient arm 23 cannot be delivered onto the crest 5 during a full rotation of 360 degrees. The non-circular cross-section of the piston rod 1 thus has to be of a kind that leaves the helical crest 5 unbroken.

In the example given in the figures and best seen in FIGS. 5 and 6, the non-circular cross-section 3 is applied as a plurality of knobs 7 extending radially from the helical crest 5 of the outer thread 2 of the piston rod 1. These knobs 7 are provided in parallel series. As further seen in FIG. 5 and in FIG. 6 a further protrusion 9 can be applied between the knobs 7. These protrusions 9 can, as disclosed, have a smaller height.

Each knob 7 has a side surface 8 as seen in FIG. 6. Together these side surfaces 8 form a longitudinal extending engagement surface making up the non-circular cross-section 3 of the piston rod 1. The further protrusion 9 also has a side surface.

Figure 7:
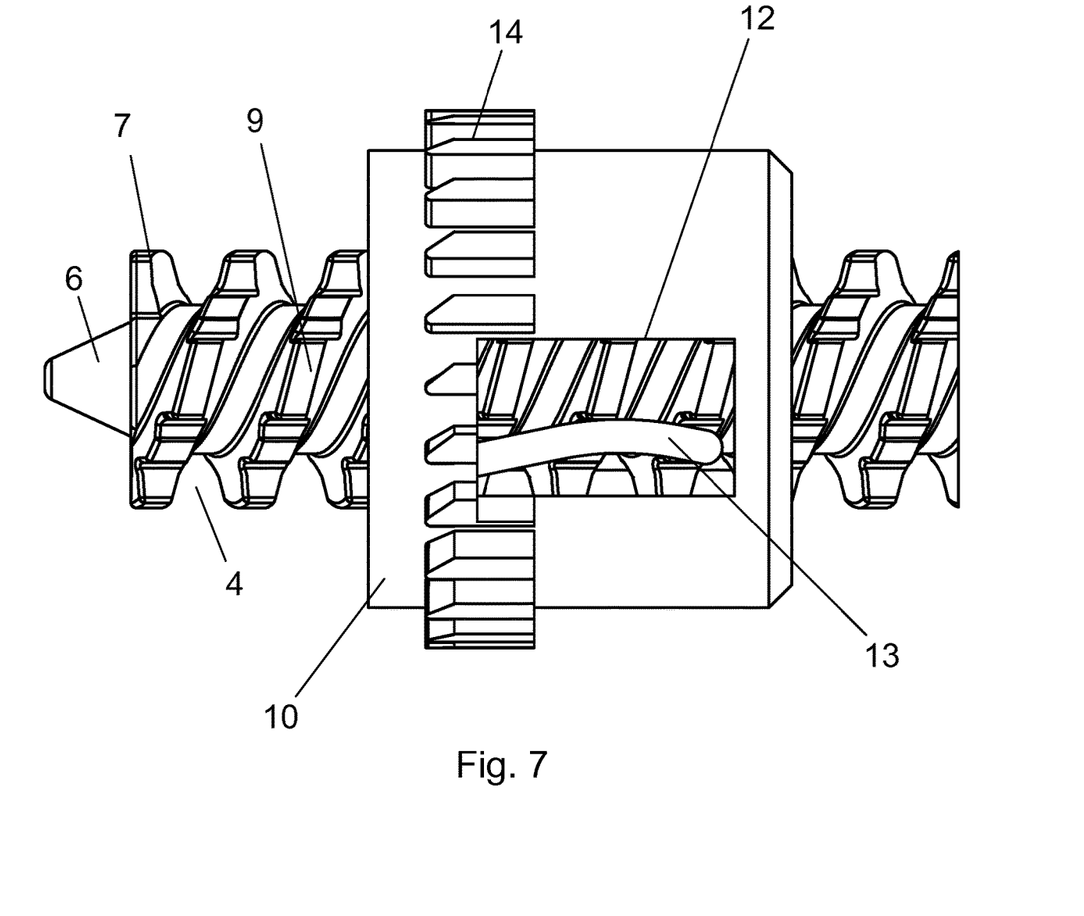
FIG. 7 show a perspective view of the engagement between the first element and the piston rod.

As shown in FIG. 7, the first element 10 preferably has a rigid flange 12 in parallel with the longitudinal direction along the centre axis X, which rigid flange 12 abuts the further protrusions 9 and a resilient arm 13 which presses the further protrusions 9 against the rigid flange 12. Alternatively, the resilient arm 13 could press the side surface of the knobs 7 against the rigid flange 12. Any number of such rigid flanges 12 and resilient arms 13 can be provided.

The principle of the resilient arms 13 is to push the piston rod 1 rotorical against the rigid flanges 12 to avoid any play between the piston rod 1 and the first element 10.

Further, the first element 10 is externally provided with a number of external protrusions 14 which again is driven by a not shown drive mechanism such as e.g. an electric motor or a spring motor during expelling of the set dose. The injection device into which the piston rod drive arrangement is implemented is preferably a torsion spring driven automatic pre-filled injection device e.g. of the type disclosed in WO 2014/060369.

The three element making up the piston drive arrangement of the present invention; the piston rod, the first element and the second element could be implemented in a large variety of different injection devices. However, the shape of the three elements as illustrated in the appending figures indicates that the preferred injection device is a pen-shaped injection device.

Some preferred embodiments have been shown in the foregoing, but it should be stressed that the invention is not limited to these, but may be embodied in other ways within the subject matter defined in the following claims. In one example, the outer thread 2 of the piston rod 1 could be asymmetrical broken by the longitudinal extending engagement surface 8 in such way the at least one of the resilient arms 23 in turn apply an axial pressure onto the piston rod 1.

The invention claimed is:

1. A piston rod drive arrangement for an injection device, comprising;
   a piston rod having an outer surface with an outer thread wherein the outer thread extends helically in a longitudinal direction along a centre line (X) and which outer surface further is provided with a longitudinal extending engagement surface such that the outer surface of the piston rod has a non-circular cross-section,
   a first element engaging the longitudinal extending engagement surface of the non-circular cross-section of the piston rod,
   a second element having an inner thread mating the outer thread of the piston rod such that the piston rod is moved in the longitudinal direction when one of the first element and the second element is rotated in relation to the other of the first element and the second element,
   a resilient arm formed as an integral part of the inner thread of the second element applies a force to the piston rod in the longitudinal direction,
   wherein the inner thread is formed from one or more thread segments, wherein at least one thread segment of the one or more thread segments terminates in the resilient arm, and
   wherein the resilient arm defines a helix angle different from a helix angle of the at least one thread segment terminating in the resilient arm and abuts a crest of the outer thread on the piston rod in order to apply the force axially onto the piston rod in the longitudinal direction.

2. A piston rod drive arrangement according to claim 1, wherein the outer thread of the piston rod is unbroken.

3. A piston rod drive arrangement according to claim 2, wherein the piston rod carries a series of knobs extending radially from the unbroken outer thread.

4. A piston rod drive arrangement according to claim 3, wherein each knob in the series extends from a top of the outer thread in a radial direction perpendicular to the longitudinal direction of the piston rod.

5. A piston rod drive arrangement according to claim 3, wherein the knobs in the series of knobs are provided following a generally straight line in parallel with the longitudinal direction of the piston rod thereby together forming the longitudinal extending engagement surface.

6. A piston rod drive arrangement according to claim 3, wherein the first element engages the longitudinal extending engagement surface of the piston rod formed by the knobs.

7. A piston rod drive arrangement according to claim 6, wherein the first element is provided with a rigid flange generally parallel with the longitudinal direction.

8. A piston rod drive arrangement according to claim 7, wherein the first element further is provided with a resiliency urging the knobs of the series of knobs rotationally against the rigid flange.

9. A piston rod drive arrangement according to claim 8, wherein the resiliency is a resilient arm which urges the longitudinal extending engagement surface made up by the knobs of the series of knobs against the rigid flange.

10. An injection device comprising:
    a housing securing a drug container, and
    a piston rod drive arrangement according to claim 1, wherein the first element is non-rotatably secured in the housing and the second element is rotatable.

11. An injection device comprising:
    a housing securing a drug container, and
    a piston rod drive arrangement according to claim 1, wherein the second element is non-rotatably secured in the housing and the first element is rotatable.

* * * * *